United States Patent [19]

Balteau et al.

[11] Patent Number: 4,790,815
[45] Date of Patent: Dec. 13, 1988

[54] HEAT STERILIZABLE PLASTIC CONTAINER WITH NON-STICK INTERIOR SURFACES

[75] Inventors: Patrick Balteau, Saint Georges; Francesco Peluso, Heverlee, both of Belgium

[73] Assignee: Baxter Travenol Laboratories, Inc., Deerfield, Ill.

[21] Appl. No.: 24,935

[22] Filed: Mar. 12, 1987

[51] Int. Cl.$^4$ .............................................. A61M 1/00
[52] U.S. Cl. ...................................... 604/29; 604/408
[58] Field of Search ............. 604/29, 28, 262, 408–410

[56] References Cited

U.S. PATENT DOCUMENTS

| | | |
|---|---|---|
| 3,416,528 | 12/1968 | Kahn . |
| 4,306,976 | 12/1981 | Bazzato ................................. 604/29 |
| 4,551,140 | 11/1985 | Shinohara ........................... 604/262 |
| 4,675,019 | 6/1987 | Bellhouse et al. .................. 604/408 |

OTHER PUBLICATIONS

Japanese Application JP59044264.
WO 84/03046 (with translation).

Primary Examiner—John D. Yasko
Attorney, Agent, or Firm—Paul C. Flattery; Daniel D. Ryan; Charles R. Mattenson

[57] ABSTRACT

A container includes facing plastic wall portions, one having a nonuniform or irregular surface finish, the other having a uniform or regular surface finish. The two differing surface finishes each have a different mean depth. The juxtaposition of these unlike wall finishes reduces or eliminates the likelihood of the walls sticking or adhering together during surface contact.

The container can undergo heat sterilization while empty without loss of function.

13 Claims, 3 Drawing Sheets

4,790,815

HEAT STERILIZABLE PLASTIC CONTAINER WITH NON-STICK INTERIOR SURFACES

FIELD OF THE INVENTION

In one aspect, the invention relates to plastic containers capable of withstanding heat sterilization processes.

In another aspect, the invention relates to heat sterilized fluid administration systems having one or more preattached empty plastic containers.

In a more particular aspect, the invention relates to a peritoneal dialysis administration system which has a preattached full container for delivering sterile fresh peritoneal dialysis solutions and a preattached empty container for receiving spent peritoneal dialysis solution and which has been heat sterilized as a single, integral unit.

BACKGROUND OF THE INVENTION

In Bazzato U.S. Pat. No. 4,306,976, a peritoneal dialysis system is discussed having preattached plastic solution bags. One of the bags is initially filled with fresh peritoneal dialysis solution to be infused into a patient. The other bag is initially empty to receive spent dialysis solution.

This arrangement is desirable for numerous reasons. First, it represents a "closed" fluid delivery system. Second, it eliminates the need for the patient to make repeated connections between the administration set and solution bags. Third, the arrangement allows the patient to disconnect the administration set and attached bags during the dialysis period while the dialysis solution dwells within the patient's peritoneal cavity. All of these benefits are particularly important to a patient practicing continuous ambulatory peritoneal dialysis, or CAPD.

Solution administration systems having preattached plastic bags can pose manufacturing difficulties, particularly with regard to sterilization. In particular, when exposed to heat sterilization, the walls of the empty plastic solution container can stick or adhere together, effectively blocking off the interior of the bag. It can be difficult to later part these walls to drain spent dialysis solution into the bag.

SUMMARY OF THE INVENTION

One of the principal objectives of this invention is to provide a plastic container which, when empty, can undergo heat sterilization without having its interior surfaces stick or adhere together.

To achieve this and other objectives, the invention provides a container having a pair of facing plastic walls. One of the plastic walls includes a nonuniformly roughened finish surface portion, having a surface roughness with a mean depth exceeding about five microns.

As used in this specification, the term "nonuniformly roughened" means a roughened surface having randomly placed irregularities, typically in the form of randomly scattered peaks and valleys, having transverse dimensions on the order of 100 to 500 microns, providing a surface that has a visible milky cast. The mean depth is measured from the peak to the valley. The nonuniformly roughened finish is impressed into the plastic wall during the extrusion process by a metal roller carrying a corresponding nonuniformly roughened finish made by sandblasting or etching. In the preferred embodiment, the nonuniformly roughened surface finish comprises a matte surface finish.

Also in accordance with the invention, the other one of the plastic walls which faces the nonuniformly roughened finish surface portion has a uniformly roughened surface finish which is different than the nonuniformly roughened surface finish and which has a surface roughness with a mean depth which exceeds the mean depth of the nonuniformly roughened finish wall portion.

As used in this specification, the term "uniformly roughened" means a surface having a nonrandom, repeated pattern, such as in the form of crossing ribs or a "weaved" taffeta appearance.

The uniform finish or "non-matte" finish of the other plastic wall may vary. However, in the preferred embodiment, the other wall carries an engraved surface finish having a mean depth in excess of about 10 microns.

It has been discovered that the juxtaposition of two different surface finishes, each with a different mean depth, minimizes the area of surface contact present when the plastic walls touch. This reduces or eliminates the likelihood that the plastic walls, when in mutual contact, will stick or adhere together. The invention thus provides a plastic container which can undergo heat sterilization without loss of function.

In one embodiment, one of the plastic walls also includes a glossy finish wall portion having optical clarity sufficient to allow inspection of the container contents.

In its preferred embodiment, the bag also includes a port tube for conducting fluid into and out of the bag. The port tube includes a portion which extends into the interior of the bag between the matte finish wall portion and the engraved finish wall portion. This inwardly extending portion of the port tube facilitates fluid transfer into the bag.

The invention also provides a fluid administration system which incorporates the container as above described. Due to the features of the invention, the entire system can be heat sterilized as a single, preassembled unit.

DESCRIPTION OF THE PREFERRED EMBODIMENT

A plastic container 10 which embodies the features of the invention is shown in FIGS. 1 through 5. While the invention is applicable for use in a diverse number of environments, in the illustrated embodiment, the container 10 is shown in association with a peritoneal dialysis administration system 12.

Figure 1:
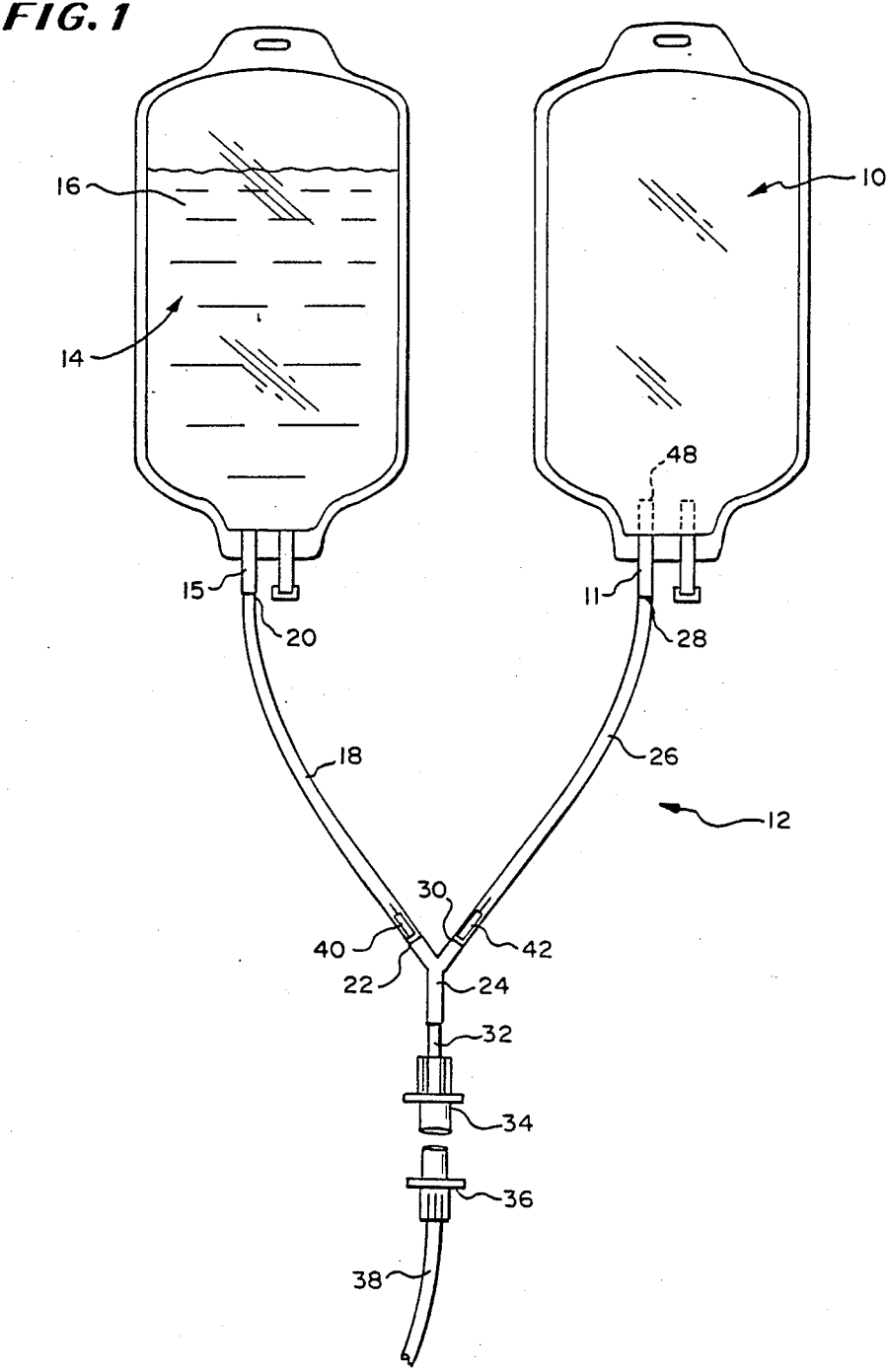
FIG. 1 is a peritoneal dialysis system with a preattached empty bag which embodies the features of the invention.
Figure 2:
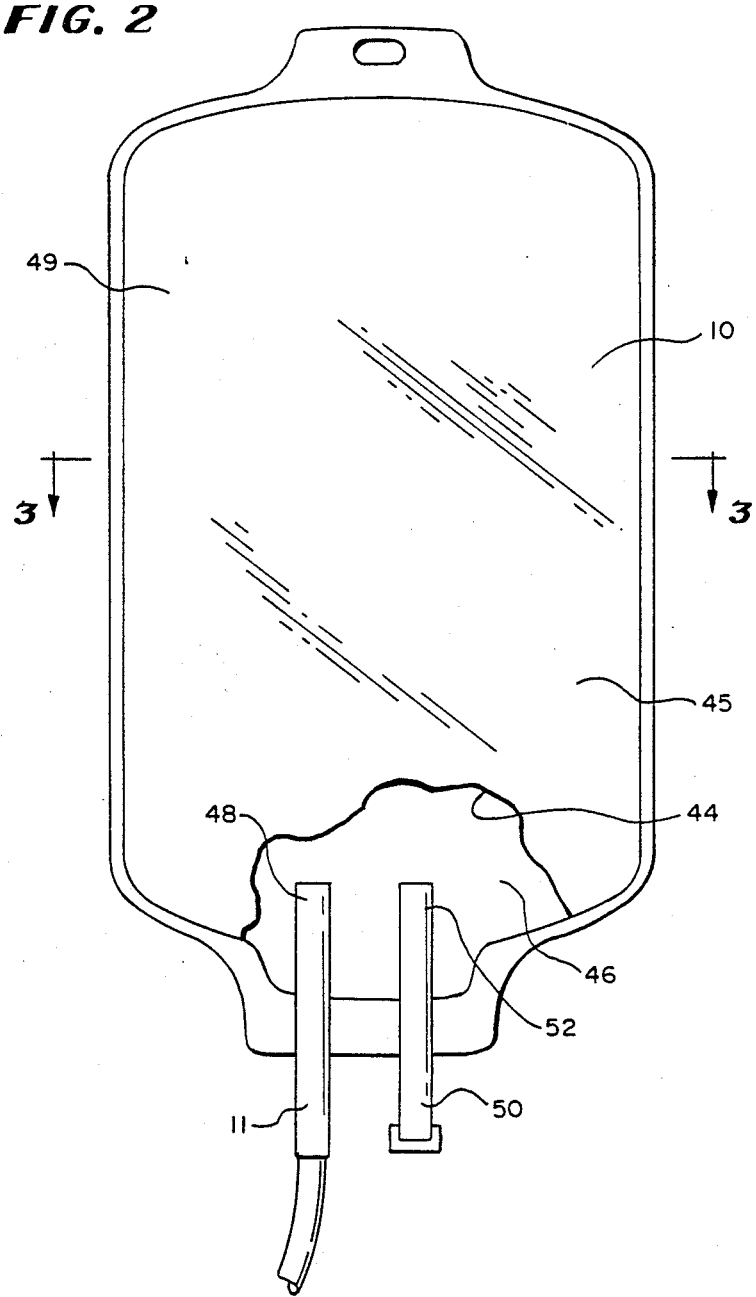
FIG. 2 is an enlarged view of the preattached empty bag shown in FIG. 1, with a portion broken away.

As shown in FIG. 1, the system 12 includes a first plastic container or bag 14 which is filled prior to use with fresh peritoneal dialysis solution 16. The first bag 14 is intended, during use, to administer fresh peritoneal dialysis solution to a patient.

A first length of tubing 18 is at one end 20 integrally connected to a part 15 of the first bag 14 and at its opposite end 22 is integrally connected to a Y-junction 24.

The system 12 also includes, as a second plastic container or bag, the bag 10 which embodies the features of the invention. The second container 10 is initially empty prior to use and is intended, during use, to receive spent dialysis solution from the patient.

A second length of tubing 26 is at one end 28 integrally connected to a port 11 of the second bag 10 and at its opposite end 30 is integrally connected to the Y-junction 24.

The plastic material from which the first and second bags are made are preferable conventional medical grade polyvinyl chloride plastic, using di-2-ethylhexylphthalate as a plasticizer. Other heat resistant medical grade plastic material, or laminates thereof, such as polyethylene or polypropylene, could also be used.

Also integrally joined to the junction 24 is a third length of tubing 32 which has at its end portion a connector 34 attachable to a connector 36 attached to a peritoneal dialysis catheter 38. By this attachment, the system 12 can be connected in fluid communication with the patient's peritoneal cavity.

The first length of tubing 18 includes a normally closed, frangible inline valve member 40 located between the junction 24 and the first bag 14. Likewise, the second length of tubing 26 includes a normally closed, frangible inline valve member 42 located between the junction 24 and the second bag 10. The frangible valves 40 and 42 can be variously constructed. In the illustrated embodiment, they are constructed as disclosed in Munsch U.S. Pat. No. 4,340,049, which is incorporated into this Specification by reference. The valve members 40 and 42 control fluid flow through the respective pathways 18 and 26 into and through the junction 24.

In use, the system 12 is connected to the peritoneal dialysis catheter 38 of a patient using the connectors 34 and 36. The inline valve member 42 is broken, and spent dialysis solution residing in the patient's peritoneal cavity is drained, via the third and second tubing lengths 32 and 26, into the empty second bag 10. Then, after externally clamping the second tubing length 26, the inline valve member 40 is broken, and fresh dialysis solution is infused, via the first and third tubing lengths 18 and 32, from the first bag 14 into the patient's peritoneal cavity.

Prior to infusion of fresh dialysis solution, the catheter 38 can be clamped and fresh dialysate solution run from the bag 14 through the junction 24 and tubing lengths 18, 26, and 32 and into the bag 10 to flush spent dialysate from the system 12.

After use, the system 12 is preferably disconnected from the patient's catheter 38 as an integral unit and discarded.

In accordance with the invention, the entire system 12 is preassembled and heat sterilized as an assembled unit prior to use by the patient. In accordance with the invention, the initially empty second bag 10 includes facing "nonstick' interior surfaces to prevent adherence of the interior wall surfaces during the heat sterilization process.

Figure 3:
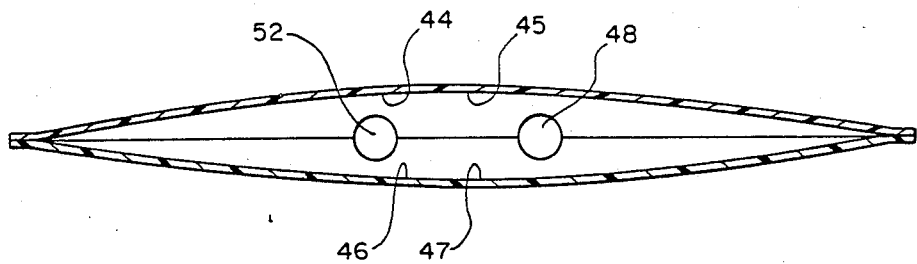
FIG. 3 is a sectional view of the bag taken generally along lines 3—3 in FIG. 2.
Figure 4:
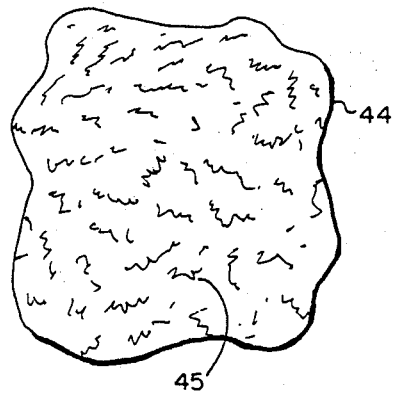
FIG. 4 is a fragmentary, highly enlarged view of the matte finish wall portion of the bag shown in FIG. 2.

More particularly, as best shown in FIG. 3, the second bag 10 includes a pair of facing flexible walls 44 and 46 which are sealed together at their peripheries. The flexible wall 44 includes a nonuniformly roughened matte finish wall portion 45 (shown in enlarged form in FIG. 4).

Figure 5:
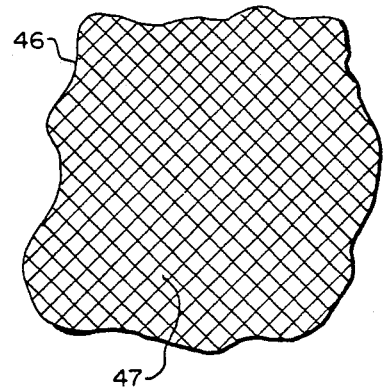
FIG. 5 is a fragmentary, highly enlarged view of the engraved finish wall portion of the bag shown in FIG. 2.

Also in accordance with the invention, the other flexible wall 46 includes a uniformly roughened engraved finish wall portion 47 shown in enlarged form in FIG. 5).

In the preferred embodiment, the matte finish wall portion 45 has a mean depth of about seven microns, while the engraved finish wall portion 47 has a mean depth of about twelve microns.

The second bag 10 also includes a glossy finish wall portion 49 located on the same flexible wall 44 as the matte finish wall portion 45. The glossy finish wall portion 49 enables the user to inspect the contents of the bag 10.

A portion 48 of the port tube 11 to which the second tubing length 26 is attached to conduct fluid into and out of the bag 10 extends into the interior of the bag 10 between the matte finish wall portion 45 and the engraved finish wall portion 47. The port tube extension 48 allows fluid to enter the bag and expand the flexible walls.

The bag 10 also includes a second port tube 50 with an extension 50 like port tube extension 48. The port tube 50 can be used to remove samples of the contents of bag 10 for testing or analysis.

The entire system 12 can be heat sterilized, such as by autoclaving, in a single operation, with the first bag 14 filled with dialysate solution and the second bag 10 empty. The juxtaposition of the matte finish surface 45 and the engraved finish surface 47 associated with the second bag 10 prevents the two flexible walls 44 and 46 from sticking or adhering to each other during sterilization.

In the illustrated and preferred embodiment, the inline valve members 40 and 42 are colored differently to allow the user to visually distinguish between the infusion leg (i.e., first tubing length 18) and the drain leg (i.e., the second tubing length 26).

Various features of the invention are set forth in the following claims.

We claim:

1. A container comprising a pair of facing flexible walls, one of said flexible walls including a nonuniformly roughened finish wall portion having a surface roughness with a mean depth exceeding about five microns, the other one of said flexible walls including a uniformly roughened finish wall portion which faces said nonuniformly roughened finish wall portion and which has a surface roughness with a mean depth greater than the mean depth of said nonuniformly roughened finish wall portion.

2. A container according to claim 1
   wherein one of said flexible walls includes a glossy finish wall portion to facilitate inspection of the container contents.

3. A container according to claim 1
   wherein said glossy finish wall portion and said nonuniformly roughened finish wall portion are located on the same flexible wall, and
   wherein said glossy finish wall portion, like said nonuniformly finish wall portion, faces said uniformly roughened finish wall portion.

4. A container according to claim 1
   wherein the mean depth of said nonuniformly roughened finish wall portion is about seven microns, and wherein the mean depth of said uniformly roughened finish wall portion is about twelve microns.

5. A container according to claim 4 wherein said uniformly roughened finish wall portion comprises an engraved finish.

6. A container according to claim 1 wherein said uniformly roughened finish wall portion comprises an engraved finish.

7. A container according to claim 4 wherein said nonuniformly roughened finish wall portion comprises a matte finish.

8. A container according to claim 1 wherein said nonuniformly roughened finish wall portion comprises a matte finish.

9. A container according to claim 1 and further including a port tube for conducting fluid into and out of said container, and wherein said port tube includes a portion which extends into the interior of said container between said nonuniformly roughened finish wall portion and said uniformly roughened finish wall portion.

10. A container according to claim 9 wherein one of said flexible walls includes a glossy finish wall portion to facilitate inspection of the container contents, said glossy finish wall portion being located away from said port tube portion.

11. A peritoneal dialysis system comprising
a first bag filled with fresh peritoneal dialysis solution, and
a second bag as defined in claims 1 or 2 or 3 or 4 or 5 or 6 or 7 or 8 or 9 or 10, said second bag intended to receive spent peritoneal dialysis solution.

12. A system according to claim 11 and further including
a first length of tubing integrally connected to said first bag,
a second length of tubing integrally connected to said second bag, and
a junction joining said first and second tubing lengths and having an end portion adapted for connection to a peritoneal dialysis catheter for instilling fresh dialysis solution from said first bag and for draining spent dialysis solution into said second bag.

13. A system according to claim 12 wherein said first length of tubing includes first inline valve means between said junction and said first bag, and
wherein said second length of tubing includes second inline valve means between said junction and said second bag.

* * * * *